United States Patent [19]

Doenges

[11] Patent Number: 4,987,584

[45] Date of Patent: Jan. 22, 1991

[54] MATERIALS INSPECTION SYSTEM USING X-RAY IMAGING

[75] Inventor: Gerhard Doenges, Heidenrod-Kemel, Fed. Rep. of Germany

[73] Assignee: Heiman GmbH, Fed. Rep. of Germany

[21] Appl. No.: 503,670

[22] Filed: Apr. 3, 1990

[30] Foreign Application Priority Data

Apr. 6, 1989 [EP] European Pat. Off. ........ 89106087.3

[51] Int. Cl.⁵ .............................................. H05G 1/64
[52] U.S. Cl. ...................................... 378/100; 378/99
[58] Field of Search .................... 378/100, 99; 358/111

[56] References Cited

U.S. PATENT DOCUMENTS 4,686,695 8/1987 Macovski .............................. 378/99

Primary Examiner—Craig E. Church
Attorney, Agent, or Firm—Hill, Van Santen, Steadman & Simpson

[57] ABSTRACT

A material inspection system, such as a baggage insepction system, uses x-ray imaging to identify organic materials such as drugs and explosives. The articles being inspected are transirradiated with x-rays having different radiation energies. From detected radiation, attenuated by the article under inspection, a materials information signal and a luminance signal are formed. The color of the monitor image is controlled by the materials information signal, and the image brightness, color saturation and white content of the image are controlled by the luminance signal. A color portrayal occurs only when the materials information signal has a sufficiently high signal-to-noise ratio.

5 Claims, 1 Drawing Sheet

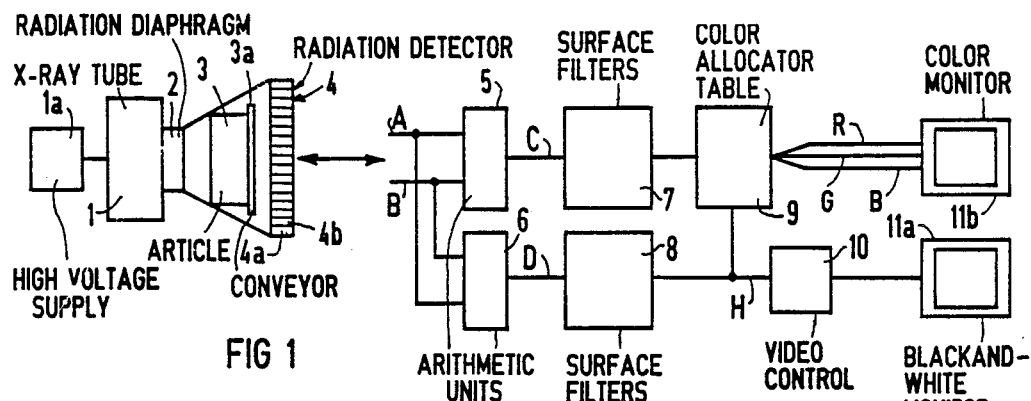
FIG 1
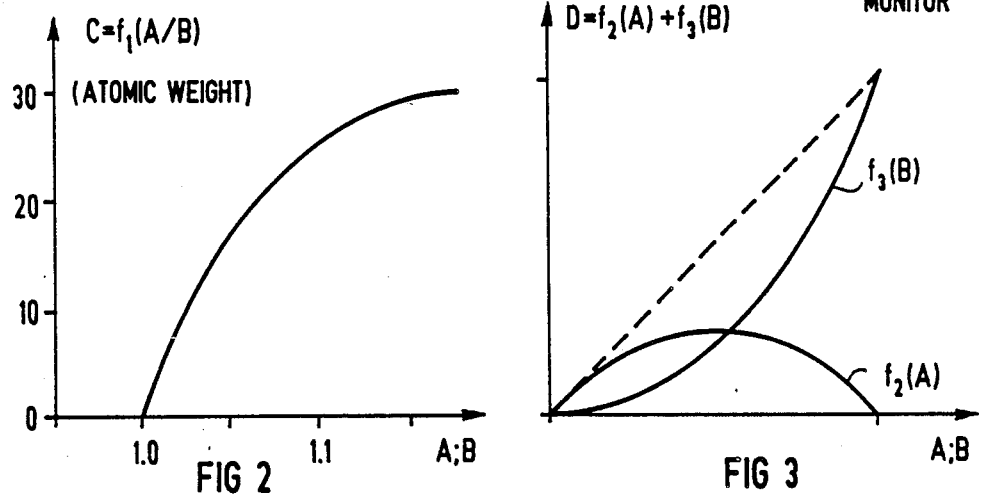
FIG 2
FIG 3
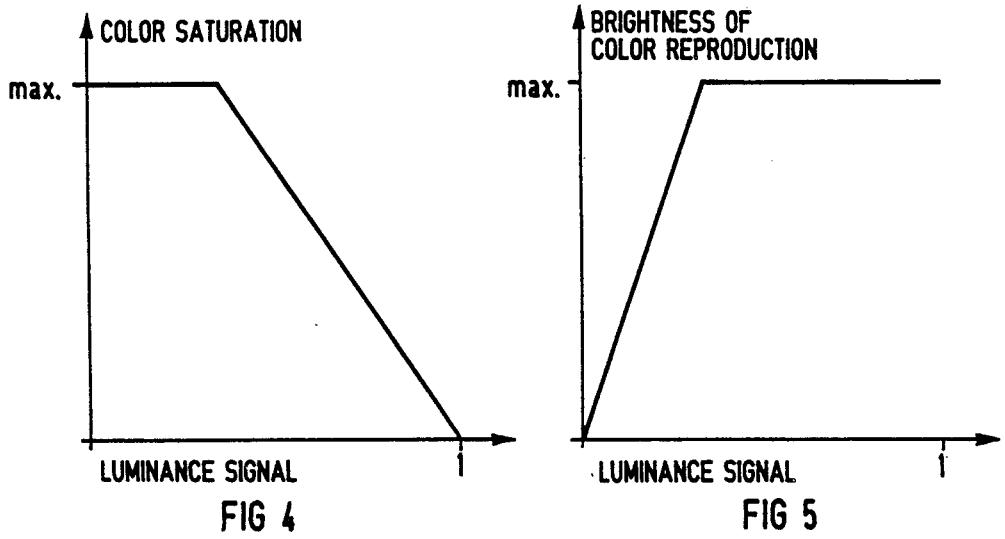
FIG 4
FIG 5

MATERIALS INSPECTION SYSTEM USING X-RAY IMAGING

BACKGROUND OF THE INVENTION

1. Field of the Invention

The present invention is directed to a materials inspection system using x-ray imaging, such as a baggage inspection system wherein articles being inspected are moved on a conveyor system through an x-ray beam. The system disclosed herein is particular suited for identifying organic material, such as drugs or explosives, in the inspected articles.

2. Description of Prior Art

Baggage inspection systems are known which generally include a conveyor for moving the articles to be inspected through a beam of x-rays. The x-ray beam is emitted on one side of the articles from an x-ray source, and a radiation detector is disposed on the opposite of the moving articles. The radiation detector is formed by a row of individual detector elements. A signal processing circuit is connected to the outputs of each of the individual detector elements, from which a visual reproduction of the contents of the inspected articles can be obtained and displayed.

It is known in medical radiology to use x-rays of different energies to conduct a radiological examination. The radiation energies are selected based on the mass attenuation coefficient and ordering number of of the chemical elements which are expected to be present in the examination subject.

By comparing at least two congruent x-ray images at different energy levels, it is possible, for example, to distinguish soft tissue (elements having a lower ordering number) from bones (elements having a higher ordering number).

SUMMARY OF THE INVENTION

It is an object of the present invention to provide a materials inspection system using x-ray imaging wherein radiation images of the article being inspected having respectively different information content can be displayed.

It is a further object of the present invention to provide such a materials inspection system wherein at least one of the displayed images provides information as to the presence of organic items in the article being inspected.

The above objects are achieved in a materials inspection system constructed in accordance with the principles of the present invention wherein the article under inspection is subjected to x-rays at different radiation energies, and the radiation attenuated by the article under inspection is converted into electrical signals which are processed in two channels. One channel forms a materials information signal and the other channel forms a luminance signal. The color of the display (monitor) picture is controlled by the materials information signal, and the image brightness, color saturation and the white content of the image are controlled by the luminance signal.

The method of transirradiating an examination subject with different radiation energies, known from medical radiology, is adapted to the requirements of materials inspection. It is thus possible to clearly distinguish organic material, such as drugs and explosives, from other materials, for example metals (weapons).

DESCRIPTION OF THE DRAWINGS

FIG. 1 is a schematic block diagram of a materials inspection system constructed in accordance with the principles of the present invention.

FIGS. 2 through 5 are graphs for explaining the operation of the system shown in FIG. 1.

DESCRIPTION OF THE PREFERRED EMBODIMENTS

A materials inspection system constructed in accordance with the principles of the present invention is schematically shown in FIG. 1. The system includes an x-ray source 1 powered by a high voltage generator 1a, and having a primary radiation diaphragm 2 so that a fan-shaped x-ray beam is emitted which transirradiates articles 3 under inspection on a conveyor path 3a. The conveyor path 3a is part of a means for conveying the articles through the fan-shaped x-ray beam, the remainder of which is well known to this skilled in the art and is not shown in detail in FIG. 1. The conveying direction proceeds perpendicularly to the plane of the drawing.

The article 3 under inspection is successively transirradiated with two different radiation energies. For this purpose, the x-ray tube voltage is switched between two levels by the high voltage generator 1a.

The attenuated x-ray beam emerging from the article 3 is incident on a radiation detector 4, which consists of a row of individual detector elements 4a, 4b, etc. Output signals A and B are respectively generated by the radiation detector 4 as a result of irradiation at the two energy levels (signal A corresponding to irradiation at one level, signal B corresponding to irradiation at the other level). The signals A and B are both supplied to two channels of a signal processing circuit. The signal processing circuit includes two arithmetic units 5 and 6, two surface filters 7 and 8, a color allocator table 9, a video control 10 and two monitors 11a and 11b. The monitor 11a is a black-and-white monitor and the monitor 11b is a color monitor for the colors red, green and blue.

The arithmetic unit 5 generates a materials information signal C in coded and digitized form from the image signals of the channels A and B corresponding to the function $f_1$:

$$C = f_1(A/B)$$

as shown in FIG. 2. The arithmetic unit 6 serves for the evaluation and summation of the image signals of the channels A and B for acquiring an aggregate luminance signal D, corresponding to the functions $f_2$ and $f_3$:

$$D = f_2(A) + f_3(B)$$

as shown in FIG. 3.

The surface filter 7 is a finite impulse response (FIR) surface filter for noise reduction. The filter 8 is a FIR surface filter for contour intensification. The output signal H of the filter 8 is the improved luminance information signal, for controlling the black-and-white monitor 11a.

The brightness-controllable color allocator table 9 has color outputs red, green and blue for controlling the color monitor 11b.

The two image signals A and B for congruent picture elements, the image signals having spectrally different information, proceed in digitized form to the arithmetic units 5 and 6. The signal A may contain information obtained from irradiation of the article 3 with higher energy, and the signal B may contain information obtained from irradiation of the article 3 with lower energy.

The arithmetic unit 5 operates on the signals A and B such that, dependent on the quotient A/B at the output, the amplitude of the output signal C is a measure of the deviation between the signals A and B. Given slight differences between A and B, a slight spectral dependency of the mass attenuation coefficient K of the article under inspection is present. This means the article includes or consists of a substance having a lower atomic weight. The quotient A/B becomes larger as the atomic weight of the irradiated substance increases. This is indicated by the graph shown in FIG. 2 for the function $C = f_1(A/B)$.

The signal C thus identifies materials information, i.e., the atomic weight, in coded form.

The arithmetic unit 6 operates on the signals A and B in the two channels so that an image signal D is obtained, which combines the information in the signals A and B. Predominantly the lower-energy components of the signal A are used in the amplitude range of low signal attenuation, and increasingly larger components of the higher-energy radiation from the signal B are used with lower amplitudes. The aggregate signal is thus:

$$D = f_2(A) + f_3(B),$$

as shown in FIG. 3.

The signal D is referred to herein as the luminance signal, because it contains the optimized gray scale information. The advantage of the calculation undertaken in the arithmetic unit 6 is that the respective signal having the maximum signal-to-noise ratio is used for acquisition of the luminance signal.

The luminance signal D and coded materials information signal C are respectively filtered in filters 8 and 7. The filter characteristic of the filters 8 and 7 differs. The luminance signal C is subjected to an edge boost for intensifying the contours in a known manner. The surface filter 8 operates two-dimensionally so that there is no dependency of the boost on the orientation of the contour.

The coded materials information signal passes through the surface filter 7 for noise reduction. In the simplest case, this is achieved by averaging a plurality of picture elements.

The signals filtered in this fashion control the color allocator table 9, which is a look-up table. The number of characteristics stored in the color allocator table 9 corresponds to the number of coded statuses of the materials information signal. Each of these statuses has a color allocated thereto, i.e., red, green or blue, with the color outputs having a defined relationship to each another. The color transitions are continuous. The luminance signal D controls the white content and the color saturation so that the image becomes white when there is no absorption. The color saturation increases with increasing absorption. Given extremely high absorption, the image brightness is additionally successively reduced until the image becomes gray, at which point no reliable materials information can be contained in the color presentation. When the luminance signal becomes zero, the image brightness also usually reaches a minimum. This is shown in FIGS. 4 and 5, wherein the curve for color saturation and the brightness of the color reproduction are respectively shown, dependent on the luminance signal.

The materials inspection system described herein thus preserves the contours (shapes) of the items in the article under inspection in the resulting image. Discrimination of the groups of materials is improved; at least three groups of materials can be identified (discriminated), with the transitions between the groups being sliding transitions. There is no loss of penetrability because, even if due to low signal amplitudes no statement about the material is possible, the contours (shapes) of the items are still imaged in a monochrome presentation. The color presentation ensues only when information about the class of materials can be extracted, i.e., only when the material has a sufficiently high signal-to-noise ratio.

Although modifications and changes may be suggested by those skilled in the art, it is the intention of the inventor to embody within the patent warranted hereon all changes and modifications as reasonably and properly come within the scope of his contribution to the art.

We claim as our invention:

1. A materials inspection system comprising:
   means for moving an article to be inspected through an x-ray beam;
   means for irradiating said article in said x-ray beam with x-ray radiation of two different energies;
   means for detecting x-rays attenuated by said article at said two different energies and for generating electrical signals corresponding thereto;
   first channel means for processing said electrical signals from said means for detecting for generating a luminance signal;
   second channel means for processing said electrical signals from said means for detecting for generating a materials information signal;
   means for generating and displaying an image of said article;
   means for controlling the color of said image based on said materials information signal; and
   means for controlling the image brightness, color saturation and white content of said image based on said luminance signal.

2. A system as claimed in claim 1 wherein said first channel means wherein said article has a range of low absorption and a range of high absorption and wherein said first channel means includes means for predominantly using electrical signals from said means for detecting corresponding to radiation of said article at a lower of said two different energies in said range of low absorption to form said luminance signal and for predominantly using electrical signals from said means for detecting corresponding to radiation of said article at a higher of said two different energies in said range of higher absorption to form said luminance signal.

3. A system as claimed in claim 1 wherein said first channel means includes an edge boosting surface filter.

4. A system as claimed in claim 1 wherein said second channel means includes a noise reduction surface filter.

5. A system as claimed in claim 1 wherein said means for generating and displaying an image includes means for generating a color image only when said materials information signal exceeds a selected signal-to-noise ratio.

* * * * *